(12) United States Patent
Peters

(10) Patent No.: US 9,540,408 B2
(45) Date of Patent: Jan. 10, 2017

(54) COBALT PRECURSORS FOR LOW TEMPERATURE ALD OR CVD OF COBALT-BASED THIN FILMS

(71) Applicant: Entegris, Inc., Billerica, MA (US)

(72) Inventor: David W. Peters, Burnet, TX (US)

(73) Assignee: Entegris, Inc., Billerica, MA (US)

( * ) Notice: Subject to any disclaimer, the term of this patent is extended or adjusted under 35 U.S.C. 154(b) by 0 days.

(21) Appl. No.: 14/430,217

(22) PCT Filed: Sep. 24, 2013

(86) PCT No.: PCT/US2013/061417
§ 371 (c)(1),
(2) Date: Mar. 21, 2015

(87) PCT Pub. No.: WO2014/052316
PCT Pub. Date: Apr. 3, 2014

(65) Prior Publication Data
US 2015/0246941 A1 Sep. 3, 2015

Related U.S. Application Data

(60) Provisional application No. 61/705,583, filed on Sep. 25, 2012.

(51) Int. Cl.
| | |
|---|---|
| *C23C 16/18* | (2006.01) |
| *C07F 15/06* | (2006.01) |
| *C23C 16/448* | (2006.01) |
| *C23C 16/455* | (2006.01) |
| *C23C 16/44* | (2006.01) |

(52) U.S. Cl.
CPC ............. *C07F 15/06* (2013.01); *C23C 16/18* (2013.01); *C23C 16/44* (2013.01); *C23C 16/4485* (2013.01); *C23C 16/45553* (2013.01)

(58) Field of Classification Search
None
See application file for complete search history.

(56) References Cited

U.S. PATENT DOCUMENTS

| | | |
|---|---|---|
| 4,361,497 A | 11/1982 | Boldt et al. |
| 7,172,967 B2 | 2/2007 | Kim et al. |
| 8,524,600 B2 | 9/2013 | Lei et al. |
| 8,765,601 B2 | 7/2014 | Lei et al. |

(Continued)

FOREIGN PATENT DOCUMENTS

| | | |
|---|---|---|
| KR | 1020080110897 A | 12/2008 |
| WO | 2007121249 A2 | 10/2007 |

(Continued)

OTHER PUBLICATIONS

Luo J of Molecular Structure Theochem V765 2006 p. 21-26.*

(Continued)

*Primary Examiner* — Joseph Miller, Jr.

(57) ABSTRACT

Cobalt silylamide and cobalt carbonyl precursors are described, which are usefully employed in vapor deposition processes, such as chemical vapor deposition and atomic layer deposition, to deposit cobalt and to form high purity cobalt-containing films at temperatures below 400° C. These precursors and processes can be utilized in the manufacture of integrated circuitry and production of devices such as microprocessors, and logic and memory chips.

6 Claims, 4 Drawing Sheets

(56) References Cited

U.S. PATENT DOCUMENTS

| | | |
|---|---|---|
| 2004/0224866 A1 | 11/2004 | Matsunaga et al. |
| 2005/0014365 A1 | 1/2005 | Moon et al. |
| 2005/0064706 A1 | 3/2005 | Kim et al. |
| 2005/0130417 A1 | 6/2005 | Ahn et al. |
| 2006/0237853 A1 | 10/2006 | Nogami |
| 2007/0077742 A1 | 4/2007 | Matsuki et al. |
| 2007/0202254 A1* | 8/2007 | Ganguli .................. C23C 16/18 427/252 |
| 2008/0132050 A1 | 6/2008 | Lavoie |
| 2009/0029036 A1 | 1/2009 | Dussarrat |
| 2009/0208637 A1 | 8/2009 | Chen et al. |
| 2009/0269507 A1 | 10/2009 | Yu et al. |
| 2012/0177845 A1 | 7/2012 | Odedra et al. |
| 2013/0251903 A1 | 9/2013 | Han |
| 2013/0260555 A1 | 10/2013 | Zope et al. |

FOREIGN PATENT DOCUMENTS

| | | |
|---|---|---|
| WO | 2007147020 A2 | 12/2007 |
| WO | 2008142653 A2 | 11/2008 |
| WO | 2013173743 A2 | 11/2013 |

OTHER PUBLICATIONS

Huo Organometallics 2004 v23 p. 765-773 I25.*

Karolyi J Organometallic Chem 2009 V694 No. 18 p. 2923-2926.*

Cunninghame, R., et al., "Electron Transfer in Organometallic Clusters. 12. Regioselective Sequential Electrocatalytic Substitution of [mu-(CF3)2C2]Co2(CO)6 by Polydentate Ligands", "Organometallics", 1987, pp. 1470-1479, vol. 6, No. 7.

McDonald, R., et al., "Gas-Phase Ligand Substitution Reactions with (OC)Fe(NO)2'-, (OC),Co(NO)'-, ( eta3-C3H5)Co(CO),'-, (C3H5)Co(C0)3'-, and CpCo(CO)2'-", "Organometallics", 1988, pp. 1806-1820, vol. 7, No. 8.

Pugh, T., et al., "Cobalt(III) Diazabutadiene Precursors for Metal Deposition: Nanoparticle and Thin Film Growth", "Inorg. Chem.", Nov. 15, 2013, pp. 13719-13729, vol. 52.

Happ, B., et al., "On the Reactivity of Acetylenes Coordinated to Cobalt. 9. Effects of Substitution and Coordination on the 13C-NMR Chemical Shifts of the sp Carbons of (.mu.2-R1C2R2)Co2(CO)6 Complexes. Molecular Structure of (.mu.2-PhC2SiPh3)Co2(CO)6", "Organometallics", Feb. 1995, pp. 809-819, vol. 14.

* cited by examiner ature atomic layer deposition (ALD) or chemical
vapor deposition (CVD) of cobalt on substrates, and to
processes for utilizing such precursors to form cobalt-
containing films, e.g., in the manufacture of integrated
circuits or other devices or products.

US 9,540,408 B2

COBALT PRECURSORS FOR LOW TEMPERATURE ALD OR CVD OF COBALT-BASED THIN FILMS

CROSS-REFERENCE TO RELATED APPLICATIONS

This application is a U.S. national phase under the provisions of 35 U.S.C. §371 of International Patent Application No. PCT/US13/61417 filed Sep. 24, 2013, which in turn claims the benefit of priority under 35 U.S.C. §119 of U.S. Provisional Patent Application No. 61/705,583 filed Sep. 25, 2013. The disclosures of such International Patent Application No. PCT/US13/61417 and U.S. Provisional Patent Application No. 61/705,583 are hereby incorporated herein by reference, in their respective entireties, for all purposes.

FIELD

The present disclosure relates to cobalt precursors for low temperature atomic layer deposition (ALD) or chemical vapor deposition (CVD) of cobalt on substrates, and to processes for utilizing such precursors to form cobalt-containing films, e.g., in the manufacture of integrated circuits or other devices or products.

DESCRIPTION OF THE RELATED ART

As integrated circuit (IC) device dimensions have continually decreased, in the use of lithography scaling methods used to shrink device geometries, new deposition materials and processes are required to maintain high-integrity, electrically interconnected thin-films. Considerations of device integrity and long-term reliability require that film corrosion be limited and that film-to-film integrity be very high. As future devices progress from two-dimensional to three-dimensional structures, such integrity and reliability are critical requirements, especially for multi-level interconnects.

Low temperature deposition of cobalt-based thin films is vital in current semiconductor device processing. Cobalt-based films are becoming increasingly important in the formation of advanced ICs, including microprocessor, logic and memory based devices. As copper interconnects have become more widely adopted, the need for corrosion inhibition has increased in importance. Towards this end, capping films and interfacial electrode materials have become more widely explored. Cobalt alloys, such as CoWP, have been widely investigated as materials for limiting copper corrosion and enhancing electro-migration in multi-level integrated devices structures.

Recent studies have explored electroless and electrochemical plating solutions for the formation of boron- or phosphorus-doped Co alloys, such as CoWB or CoWP, respectively. Several papers have described the successful electroless plating of CoWP as a thin-film barrier layer for copper-plated interconnections. These layers provide good electrical properties while also reducing auto-oxidation and corrosion of the encapsulated copper features.

Research and development into novel chemical precursors, used to deposit cobalt-based thin-films at low temperatures from the gas-phase, is a major focus for material suppliers and device makers. The real challenge for material suppliers is in balancing the precursor thermal stability and volatility, while achieving high-purity films at relatively low processing temperatures. The precursors must be stable towards transport and handling at room temperature, while decomposing into high-purity cobalt films upon thermal or chemical decomposition at deposition temperatures. A number of precursors for cobalt have been previously reported for both CVD and ALD, such as di-cobalt octacarbonyl, cobalt nitrosyl complexes, and β-diketonates of cobalt (II) and cobalt (III).

For most device related processes, thin films are preferably deposited at temperatures below 400° C., and more preferably below 300° C. To achieve these low deposition temperatures, chemical precursors are required that can decompose cleanly to the desired metal films at correspondingly low temperatures (<400° C.). To achieve low temperature, highly conformal films, the industry is also exploring ALD methods for film deposition. These deposition processes can rely on oxidizing co-reactants, such as $O_2$, $O_3$, $N_2O$, or water, or reducing co-reactants, such as $H_2$, $NH_3$, and other reducing species known to produce cobalt, cobalt alloy or cobalt nitride thin films. In some cases, a second metal-containing co-reactant is used to produce Co—W alloy films, such as CoW, CoWP or CoWB.

The art continues to seek new low-cost, thermally stable precursors for forming conformal cobalt-containing thin films, particularly in the formation of such films in high-aspect ratio features as required for future IC devices.

SUMMARY

The present disclosure relates to cobalt precursors useful in low temperature ALD or CVD processes for depositing cobalt on substrates, and to processes employing such precursors for cobalt deposition, e.g., for manufacturing ICs or other devices or products.

In one aspect, the disclosure relates to a method of depositing cobalt, comprising volatilizing a cobalt precursor to form precursor vapor, and depositing cobalt from the precursor vapor in a vapor deposition process, wherein the cobalt precursor is selected from the group consisting of:

(a) cobalt hexacarbonyl complex precursors of the formula:

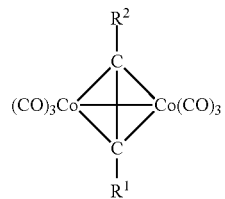

wherein $R^1$ and $R^2$ may be the same as or different from one another, and each is independently selected from among H, $C_1$-$C_4$ alkyl, silyl-substituted alkyl, dialkylamide, ethylene, acetylene, alkynes, substituted alkenes, $C_1$-$C_4$ substituted alkynes, silylalkyl, silylamide, trimethylsilyl, trialkylsilyl-substituted alkynes, and trialkylsilylamido-substituted alkynes, and wherein $R^1$ and $R^2$ are not both H;

(b) cobalt silylamide precursors;

(c) cobalt (0) carbonyl complex precursors including at least one ligand selected from the group consisting of alkenes, allenes, alkynes, and Lewis base ligands;

(d) cobalt hexacarbonyl dinitrile precursors of the formula [RN≡C—Co(CO)$_3$]$_2$, wherein R is independently selected from among H, $C_1$-$C_4$ alkyl, silyl-substituted alkyl, dialkylamide, ethylene, acetylene, alkynes, substituted alkenes, $C_1$-$C_4$ substituted alkynes, silylalkyl, silylamide, trimethylsilyl, trialkylsilyl-substituted alkynes, and trialkylsilylamido-substituted alkynes; and (e) cobalt dicarbonyl nitrile precursors of the formula (CO)$_2$CoN≡O(C≡NR) wherein R is independently selected from among H, C$_1$-C$_4$ alkyl, silyl-substituted alkyl, dialkylamide, ethylene, acetylene, alkynes, substituted alkenes, C$_1$-C$_4$ substituted alkynes, silylalkyl, silylamide, trimethylsilyl, trialkylsilyl-substituted alkynes, and trialkylsilylamido-substituted alkynes.

In another aspect, the disclosure relates to a method of providing for use in a vapor deposition process for depositing cobalt, a packaged cobalt precursor, wherein the cobalt precursor is selected from the group consisting of:

(a) cobalt hexacarbonyl complex precursors of the formula:

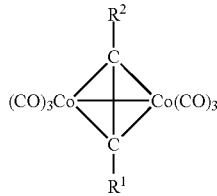

10 wherein R$^1$ and R$^2$ may be the same as or different from one another, and each is independently selected from among H, C$_1$-C$_4$ alkyl, silyl-substituted alkyl, dialkylamide, ethylene, acetylene, alkynes, substituted alkenes, C$_1$-C$_4$ substituted alkynes, silylalkyl, silylamide, trimethylsilyl, trialkylsilyl-substituted alkynes, and trialkylsilylamido-substituted alkynes, and wherein R$^1$ and R$^2$ are not both H;

(b) cobalt silylamide precursors;

(c) cobalt (0) carbonyl complex precursors including at least one ligand selected from the group consisting of alkenes, allenes, alkynes, and Lewis base ligands;

(d) cobalt hexacarbonyl dinitrile precursors of the formula [RN≡C—Co(CO)$_3$]$_2$, wherein R is independently selected from among H, C$_1$-C$_4$ alkyl, silyl-substituted alkyl, dialkylamide, ethylene, acetylene, alkynes, substituted alkenes, C$_1$-C$_4$ substituted alkynes, silylalkyl, silylamide, trimethylsilyl, trialkylsilyl-substituted alkynes, and trialkylsilylamido-substituted alkynes; and (e) cobalt dicarbonyl nitrile precursors of the formula (CO)$_2$CoN≡O(C≡NR) wherein R is independently selected from among H, C$_1$-C$_4$ alkyl, silyl-substituted alkyl, dialkylamide, ethylene, acetylene, alkynes, substituted alkenes, C$_1$-C$_4$ substituted alkynes, silylalkyl, silylamide, trimethylsilyl, trialkylsilyl-substituted alkynes, and trialkylsilylamido-substituted alkynes.

In a further aspect, the disclosure relates to a cobalt precursor selected from the group consisting of:

(a) cobalt hexacarbonyl complex precursors of the formula:

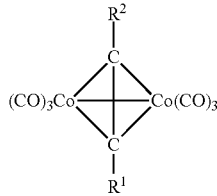

wherein R$^1$ and R$^2$ may be the same as or different from one another, and each is independently selected from among H, C$_1$-C$_4$ alkyl, silyl-substituted alkyl, dialkylamide, ethylene, acetylene, alkynes, substituted alkenes, C$_1$-C$_4$ substituted alkynes, silylalkyl, silylamide, trimethylsilyl, trialkylsilyl-substituted alkynes, and trialkylsilylamido-substituted alkynes, and wherein R$^1$ and R$^2$ are not both H;

(b) cobalt (0) carbonyl complex precursors including at least one ligand selected from the group consisting of alkenes, allenes, alkynes, and Lewis base ligands;

(c) cobalt hexacarbonyl dinitrile precursors of the formula [RN≡C—Co(CO)$_3$]$_2$, wherein R is independently selected from among H, C$_1$-C$_4$ alkyl, silyl-substituted alkyl, dialkylamide, ethylene, acetylene, alkynes, substituted alkenes, C$_1$-C$_4$ substituted alkynes, silylalkyl, silylamide, trimethylsilyl, trialkylsilyl-substituted alkynes, and trialkylsilylamido-substituted alkynes; and (d) cobalt dicarbonyl nitrile precursors of the formula (CO)$_2$CoN≡O(C≡NR) wherein R is independently selected from among H, C$_1$-C$_4$ alkyl, silyl-substituted alkyl, dialkylamide, ethylene, acetylene, alkynes, substituted alkenes, C$_1$-C$_4$ substituted alkynes, silylalkyl, silylamide, trimethylsilyl, trialkylsilyl-substituted alkynes, and trialkylsilylamido-substituted alkynes.

Other aspects, features and embodiments of the disclosure will be more fully apparent from the ensuing disclosure and appended claims.

DETAILED DESCRIPTION

Figure 1:
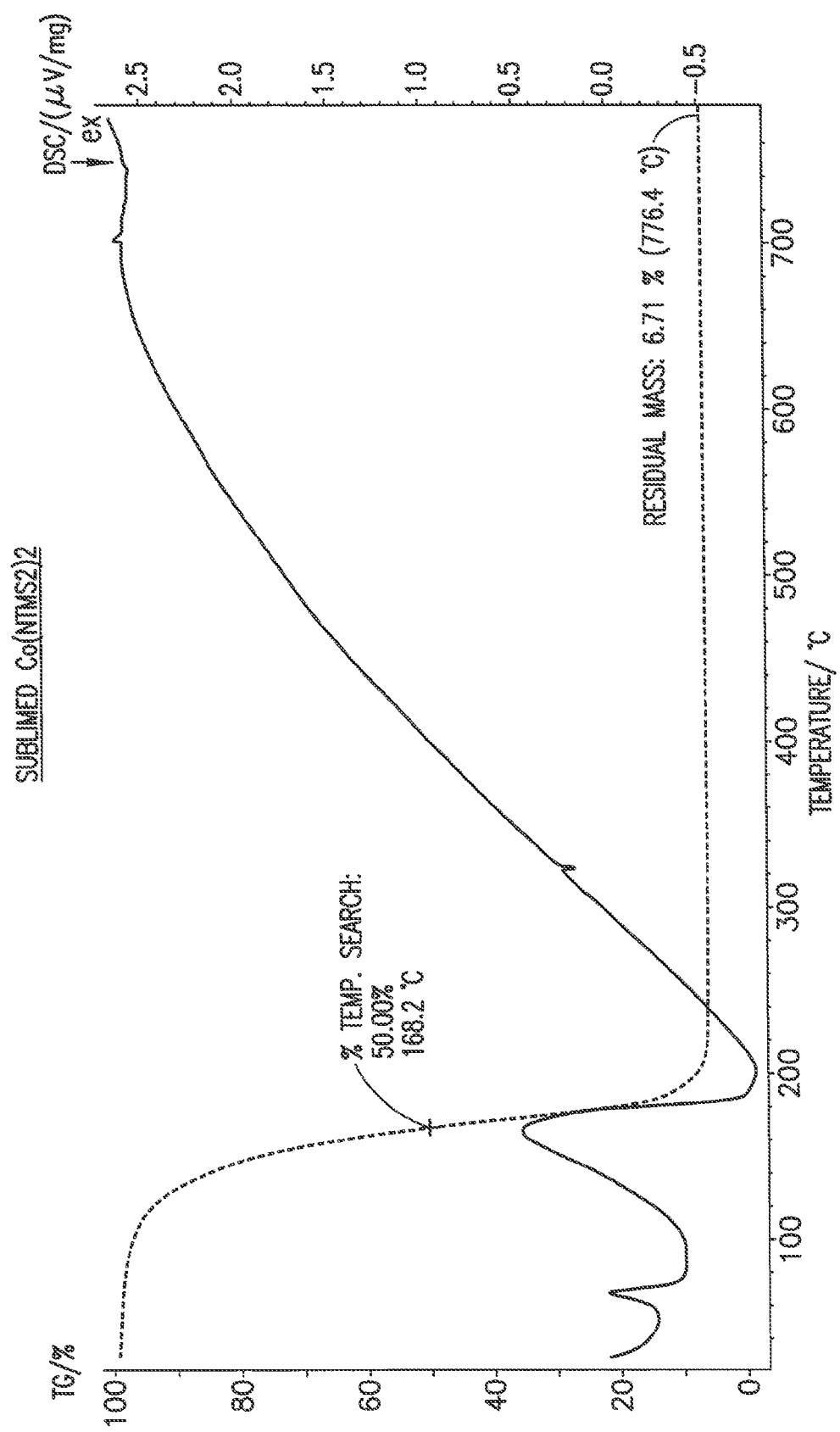
FIG. 1 is a thermal analysis (TGA/DSC) plot for bis(trimethylsilyl)amido cobalt (II).

The present disclosure relates to cobalt precursors and vapor deposition processes utilizing same.

As used herein and in the appended claims, the singular forms "a", "and", and "the" include plural referents unless the context clearly dictates otherwise.

As used herein, the term "film" refers to a layer of deposited material having a thickness below 1000 micrometers, e.g., from such value down to atomic monolayer thickness values. In various embodiments, film thicknesses of deposited material layers in the practice of the invention may for example be below 100, 10, or 1 micrometers, or in various thin film regimes below 200, 100, or 50 nanometers, depending on the specific application involved. As used herein, the term "thin film" means a layer of a material having a thickness below 1 micrometer.

As used herein, the identification of a carbon number range, e.g., in C$_1$-C$_{12}$ alkyl, is intended to include each of the component carbon number moieties within such range, so that each intervening carbon number and any other stated or intervening carbon number value in that stated range, is encompassed, it being further understood that sub-ranges of carbon number within specified carbon number ranges may independently be included in smaller carbon number ranges, within the scope of the disclosure, and that ranges of carbon numbers specifically excluding a carbon number or numbers are included in the disclosure, and sub-ranges excluding either or both of carbon number limits of specified ranges are also included in the disclosure. Accordingly, $C_1$-$C_{12}$ alkyl is intended to include methyl, ethyl, propyl, butyl, pentyl, hexyl, heptyl, octyl, nonyl, decyl, undecyl and dodecyl, including straight chain as well as branched groups of such types. It therefore is to be appreciated that identification of a carbon number range, e.g., $C_1$-$C_{12}$, as broadly applicable to a substituent moiety, enables, in specific embodiments of the disclosure, the carbon number range to be further restricted, as a sub-group of moieties having a carbon number range within the broader specification of the substituent moiety. By way of example, the carbon number range e.g., $C_1$-$C_{12}$ alkyl, may be more restrictively specified, in particular embodiments of the invention, to encompass sub-ranges such as $C_1$-$C_4$ alkyl, $C_2$-$C_8$ alkyl, $C_2$-$C_4$ alkyl, $C_3$-$C_5$ alkyl, or any other sub-range within the broad carbon number range. In other words, a carbon number range is deemed to affirmatively set forth each of the carbon number species in the range, as to the substituent, moiety, or compound to which such range applies, as a selection group from which specific ones of the members of the selection group may be selected, either as a sequential carbon number sub-range, or as specific carbon number species within such selection group.

The same construction and selection flexibility is applicable to stoichiometric coefficients and numerical values specifying the number of atoms, functional groups, ions or moieties, as to specified ranges, numerical value constraints (e.g., inequalities, greater than, less than constraints), as well as oxidation states and other variables determinative of the specific form, charge state, and composition applicable to chemical entities within the broad scope of the present disclosure.

"Alkyls" as used herein include, but are not limited to, methyl, ethyl, propyl, isopropyl, butyl, s-butyl, t-butyl, pentyl and isopentyl and the like. "Aryls" as used herein includes hydrocarbons derived from benzene or a benzene derivative that are unsaturated aromatic carbocyclic groups of from 6 to 10 carbon atoms. The aryls may have a single or multiple rings. The term "aryl" as used herein also includes substituted aryls. Examples include, but are not limited to phenyl, naphthyl, xylene, phenylethane, substituted phenyl, substituted naphthyl, substituted xylene, substituted phenylethane and the like. "Cycloalkyls" as used herein include, but are not limited to cyclopropyl, cyclobutyl, cyclopentyl, cyclohexyl and the like. In all chemical formulae herein, a range of carbon numbers will be regarded as specifying a sequence of consecutive alternative carbon-containing moieties, including all moieties containing numbers of carbon atoms intermediate the endpoint values of carbon number in the specific range as well as moieties containing numbers of carbon atoms equal to an endpoint value of the specific range, e.g., $C_1$-$C_6$, is inclusive of $C_1$, $C_2$, $C_3$, $C_4$, $C_5$ and $C_6$, and each of such broader ranges may be further limitingly specified with reference to carbon numbers within such ranges, as sub-ranges thereof. Thus, for example, the range $C_1$-$C_6$ would be inclusive of and can be further limited by specification of sub-ranges such as $C_1$-$C_3$, $C_1$-$C_4$, $C_2$-$C_6$, $C_4$-$C_6$, etc. within the scope of the broader range.

The disclosure, as variously set out herein in respect of features, aspects and embodiments thereof, may in particular implementations be constituted as comprising, consisting, or consisting essentially of, some or all of such features, aspects and embodiments, as well as elements and components thereof being aggregated to constitute various further implementations of the disclosure. The disclosure is described herein in various embodiments, and with reference to various features and aspects. The disclosure contemplates such features, aspects and embodiments in various permutations and combinations, as being within the scope of the disclosure. The disclosure may therefore be specified as comprising, consisting or consisting essentially of, any of such combinations and permutations of these specific features, aspects and embodiments, or a selected one or ones thereof.

In one aspect, the disclosure relates to a method of depositing cobalt, comprising volatilizing a cobalt precursor to form precursor vapor, and depositing cobalt from the precursor vapor in a vapor deposition process, wherein the cobalt precursor is selected from the group consisting of:

(a) cobalt hexacarbonyl complex precursors of the formula:

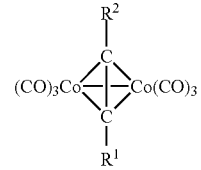

wherein $R^1$ and $R^2$ may be the same as or different from one another, and each is independently selected from among H, $C_1$-$C_4$ alkyl, silyl-substituted alkyl, dialkylamide, ethylene, acetylene, alkynes, substituted alkenes, $C_1$-$C_4$ substituted alkynes, silylalkyl, silylamide, trimethylsilyl, trialkylsilyl-substituted alkynes, and trialkylsilylamido-substituted alkynes, and wherein $R^1$ and $R^2$ are not both H;

(b) cobalt silylamide precursors;

(c) cobalt (0) carbonyl complex precursors including at least one ligand selected from the group consisting of alkenes, allenes, alkynes, and Lewis base ligands;

(d) cobalt hexacarbonyl dinitrile precursors of the formula $[RN\equiv C-Co(CO)_3]_2$, wherein R is independently selected from among H, $C_1$-$C_4$ alkyl, silyl-substituted alkyl, dialkylamide, ethylene, acetylene, alkynes, substituted alkenes, $C_1$-$C_4$ substituted alkynes, silylalkyl, silylamide, trimethylsilyl, trialkylsilyl-substituted alkynes, and trialkylsilylamido-substituted alkynes; and (e) cobalt dicarbonyl nitrile precursors of the formula $(CO)_2CoN\equiv O(C\equiv NR)$ wherein R is independently selected from among H, $C_1$-$C_4$ alkyl, silyl-substituted alkyl, dialkylamide, ethylene, acetylene, alkynes, substituted alkenes, $C_1$-$C_4$ substituted alkynes, silylalkyl, silylamide, trimethylsilyl, trialkylsilyl-substituted alkynes, and trialkylsilylamido-substituted alkynes.

In such method, the vapor deposition process may comprise a chemical vapor deposition (CVD) process, a digital CVD process, an atomic layer deposition (ALD) process, or other suitable vapor deposition process.

The vapor deposition process is advantageously conducted at temperature below 400° C., e.g., a temperature of 300° C. or less.

One class of precursors of the present disclosure includes cobalt hexacarbonyl complex precursors of the formula:

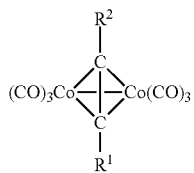

wherein $R^1$ and $R^2$ may be the same as or different from one another, and each is independently selected from among H, $C_1$-$C_4$ alkyl, silyl-substituted alkyl, dialkylamide, ethylene, acetylene, alkynes, substituted alkenes, $C_1$-$C_4$ substituted alkynes, silylalkyl, silylamide, trimethylsilyl, trialkylsilyl-substituted alkynes, and trialkylsilylamido-substituted alkynes, and wherein $R^1$ and $R^2$ are not both H. In an illustrative precursor of such formula, $R^1$=H and $R^2$=Si(Me)$_3$.

Another class of cobalt precursors of the present disclosure includes cobalt silylamide precursors. Cobalt (II) silylamides have been reported in the literature, but are not described as precursors for use in CVD or ALD processes. See, for example, H. Bürger and U. Wannagat, "Silylamido-Derivate von Eisen and Kobalt". *Monatshefte für Chemie*, 94, 1007-1012, 1963, and J. Chem. Soc. Dalton Trans., 1982, 887). To our knowledge, cobalt silylamides have not been used or proposed for deposition of any cobalt-containing films. We have synthesized cobalt silylamides compounds and examined their material properties with respect to volatility and thermal stability, and confirmed that they are useful precursors for the low temperature ALD and low temperature CVD deposition of cobalt containing films.

These cobalt silylamide precursors exhibit good thermal stability, good volatility and thermal reactivity at substrate temperatures suitable for deposition. The chemical reactivity of the precursors allows for effective film growth at low substrate temperatures at which traditional cobalt precursor materials are inert and thus, exhibit little to no deposition behavior. The thermal stability of these cobalt silylamide precursors ensures process stability, since they do not undergo undesired decomposition during delivery and film growth processes. Their good thermal stability also enhances step coverage and conformality in complex, high-aspect ratio structures, since the precursor is evenly adsorbed on 3D surfaces, prior to cobalt film formation.

Cobalt (II) silylamides of the present disclosure include compounds of the formula

wherein:
each R is independently selected from among H, $C_1$-$C_4$ alkyl, and $C_1$-$C_4$ cycloalkyl; and
a is 2 or 3, depending on the oxidation state of cobalt,
as well as compounds of the formula

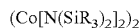

wherein:
each R is independently selected from among H, $C_1$-$C_4$ alkyl, and $C_1$-$C_4$ cycloalkyl; and the oxidation state of cobalt is 2.

Thus, the cobalt silylamide precursor may be constituted as having two or three trimethylsilylamido ligands coordinated to each cobalt atom in the precursor. In some embodiments of the cobalt silylamide precursors, substituent(s) such as H, $C_1$-$C_4$ alkyl, and $C_1$-$C_4$ cycloalkyl may be present on a silicon atom of a silylamide moiety of the precursor.

In one preferred cobalt silylamide precursor of the formula Co[N{SiR$_3$}$_2$]$_a$, R=methyl. In the dimer compounds of the formula (Co[N{SiR$_3$}$_2$]$_2$)$_2$, R also may be methyl, corresponding to (Co[N{Si(CH$_3$)$_3$}$_2$]$_2$)$_2$, bis (trimethylsilyl) amido cobalt (II), having the structure:

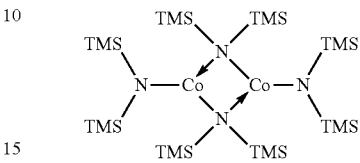

wherein:
TMS is trimethylsilyl.

The foregoing cobalt precursors are readily synthesized from common starting materials and isolated in good yields, within the skill of the art, based on the disclosure herein. These precursors have low melting point, good thermal stability, and useful vapor pressures (volatility) for vapor deposition of cobalt by processes such as CVD and ALD.

The thermal analysis (TGA/DSC) plot for bis (trimethylsilyl)amido cobalt (II) is shown in FIG. 1, including graphs of thermogravimetric analysis and of differential scanning calorimetry data for such precursor. Such plot shows bis (trimethylsilyl) amido cobalt (II) to have a melting point of 64° C. with efficient thermal transport (6.7% residual mass) and a $t_{50}$ value=168° C. ($t_{50}$ is the temperature corresponding to transport of half of the precursor material). Thermal stability of such bis (trimethylsilyl)amido cobalt (II) precursor was confirmed using proton NMR spectroscopy.

Such representative precursor bis (trimethylsilyl)amido cobalt (II) can be delivered to a deposition reactor at high flux at temperature in a range of from 60 to 100° C. and at pressure on the order of 1 Torr. At a delivery temperature above 64° C., bis (trimethylsilyl)amido cobalt (II) is a liquid, thereby facilitating precursor delivery by liquid delivery techniques. In addition, bis (trimethylsilyl)amido cobalt (II) is resistant to thermal decomposition, thereby ensuring process stability by limiting undesired decomposition of the cobalt (II) silylamides during delivery and deposition.

Another class of cobalt precursors of the present disclosure comprise cobalt (0) carbonyl complex precursors including at least one ligand selected from the group consisting of alkenes, allenes, alkynes, and Lewis base ligands.

Figure 2:
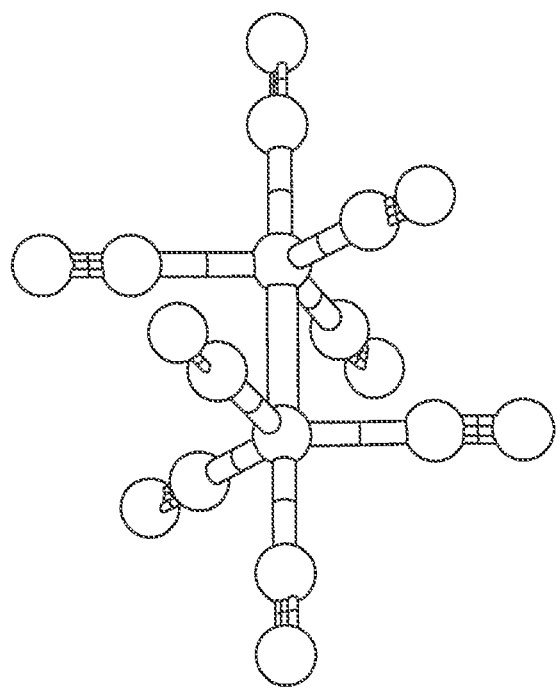
FIG. 2 is a schematic depiction of a di-cobalt octacarbonyl structure, in which all eight carbonyl groups are free pendant groups.
Figure 3:
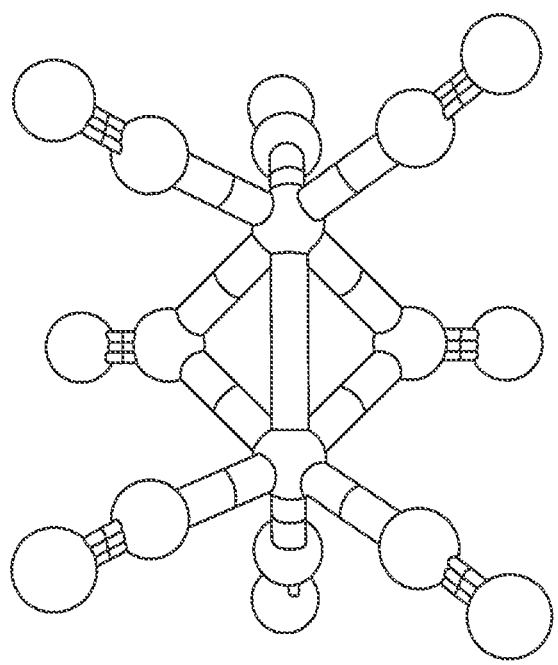
FIG. 3 is a schematic depiction of a di-cobalt octacarbonyl structure, including two bridging carbonyl groups and six free pendant group carbonyl moieties.

Cobalt precursors of such type may be formed by reaction of cobalt carbonyl compounds with a suitable ligand source compound. For example, the disclosure contemplates di-cobalt octacarbonyl derivatives formed from di-cobalt octacarbonyl of the structure shown in FIG. 2, in which all eight carbonyl groups are free pendant groups, or di-cobalt octacarbonyl derivatives formed from di-cobalt octacarbonyl of the structure shown in FIG. 3, including two bridging carbonyl groups and six free pendant group carbonyl moieties. These di-cobalt octacarbonyl compounds can be reacted with reactive species such as alkenes, allenes, alkynes, and/or Lewis base ligands, to form mixed ligand cobalt carbonyl complexes. The reaction typically eliminates two carbonyl groups.

Figure 4:
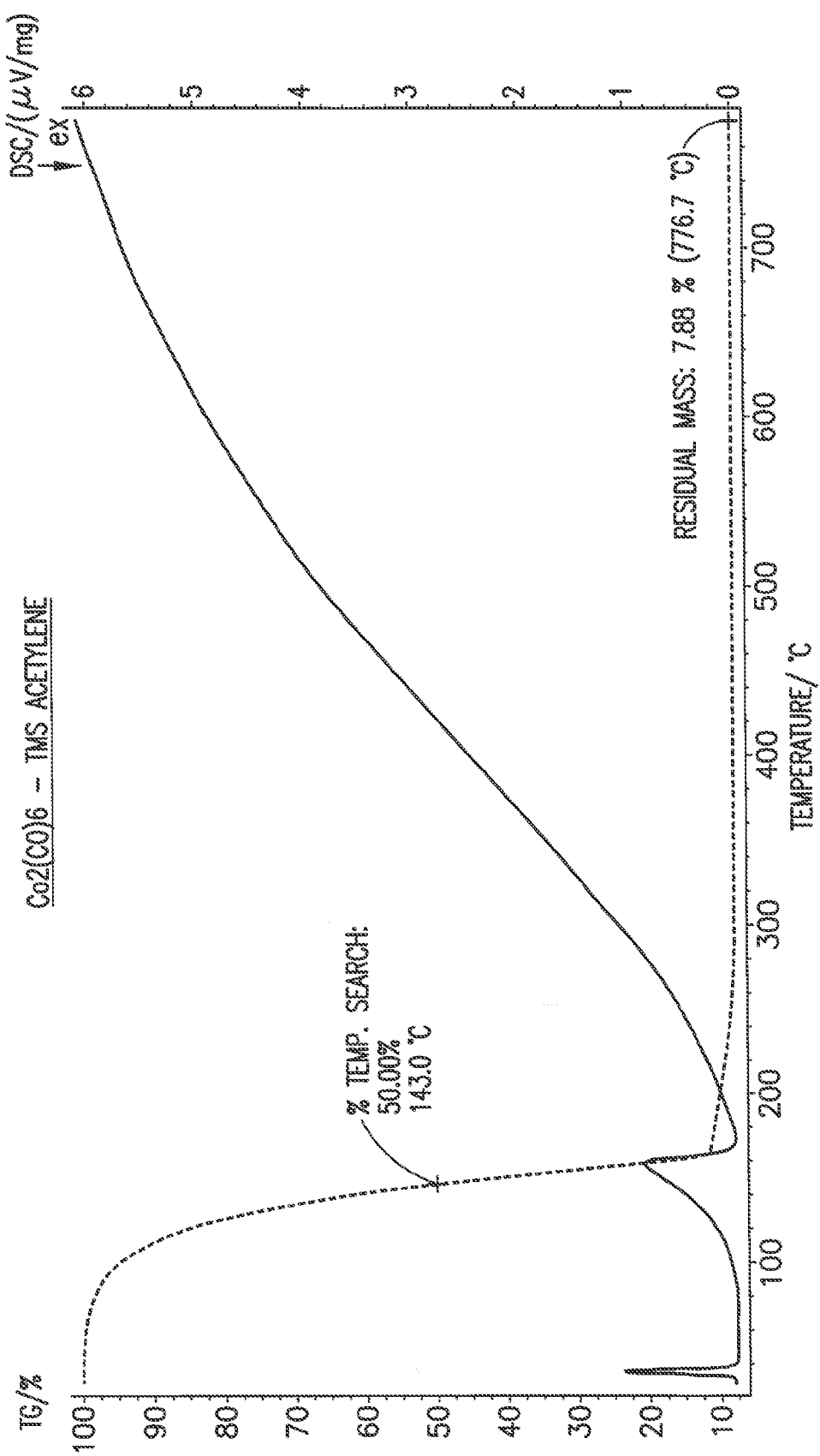
FIG. 4 is a thermal analysis (TGA/DSC) plot for dicobalt hexacarbonyl (trimethylsilylacetylene).

An illustrative example of such mixed ligand di-cobalt carbonyl precursor is the acetylene substituted dicobalt hexacarbonyl precursor, dicobalt hexacarbonyl (trimethylsilylacetylene). The results of thermal analysis of such cobalt precursor are shown in FIG. 4, demonstrating that dicobalt hexacarbonyl (trimethylsilylacetylene) is a useful precursor for deposition of cobalt containing films. Di-cobalt hexacarbonyl (trimethylsilylacetylene) has a melting point of 35° C., good thermal stability and efficient transport characterized by a t50 value centered at 143° C. The residual mass for this precursor, as measured by thermogravimetric analysis, was 7.8% at elevated temperature greater than 300° C.

Another class of cobalt precursors of the present disclosure includes cobalt hexacarbonyl dinitrile precursors of the formula [RN≡C—Co(CO)$_3$]$_2$, wherein R is independently selected from among H, $C_1$-$C_4$ alkyl, silyl-substituted alkyl, dialkylamide, ethylene, acetylene, alkynes, substituted alkenes, $C_1$-$C_4$ substituted alkynes, silylalkyl, silylamide, trimethylsilyl, trialkylsilyl-substituted alkynes, and trialkylsilylamido-substituted alkynes. An illustrative example of such precursor is [$^t$BuNC Co(CO)$_3$]$_2$,

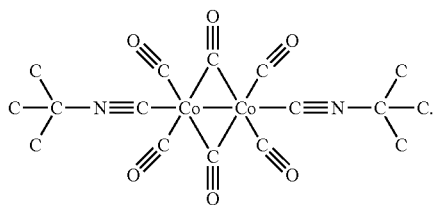

This precursor is a solid at 25° C.

A further class of cobalt precursors of the present disclosure includes cobalt dicarbonyl nitrile precursors of the formula (CO)$_2$CoN═O(C≡NR) wherein R is independently selected from among H, $C_1$-$C_4$ alkyl, silyl-substituted alkyl, dialkylamide, ethylene, acetylene, alkynes, substituted alkenes, $C_1$-$C_4$ substituted alkynes, silylalkyl, silylamide, trimethylsilyl, trialkylsilyl-substituted alkynes, and trialkylsilylamido-substituted alkynes. An illustrative precursor of such type is (CO)$_2$CoN═O(CN$^t$Bu),

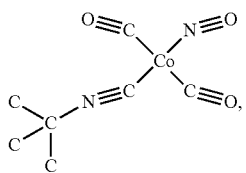

which is a free flowing liquid at 25° C.

The cobalt precursors described herein can be used to deposit high-purity cobalt thin-films and alloys via CVD, digital CVD, and ALD. Co-reactants can be used to deposit specific thin-film compositions. For example, water, $O_2$, $O_3$ and $N_2O$ can be used to react with cobalt precursors to form $CoO_x$ films. $H_2$, $NH_3$ or alkylamines with $H_2$ can be used to form Co or $CoN_x$ films. Carbon sources, such as methane or ethane can be used to form CoC films. Cobalt silicate films can be used as high k materials and require co-reaction with a silicon species. In some cases, the cobalt silylamides or carbonyl complexes containing silicon ligands, can be used advantageously to form CoSiOx films in an oxidizing environment. Other film growth co-reactants will be appreciated by those skilled in the art of thin-film formation methods, based on the disclosure herein.

Thus, the disclosure contemplates the use of precursors as variously described herein to form cobalt-containing films comprising at least one of oxygen, nitrogen, carbon and silicon, e.g., in a vapor deposition process in which the cobalt precursor and the film contain silicon. The vapor deposition process may be conducted to form a cobalt-containing film comprising at least one of oxygen, nitrogen, carbon and silicon, e.g., wherein the film comprises cobalt oxide, and the co-reactant comprises at least one of water, $O_2$, $O_3$ and $N_2O$, or wherein the film comprises cobalt nitride, and the co-reactant comprises at least one of ammonia and amine, e.g., an alkylamine, or wherein the film comprises cobalt carbide, and the co-reactant comprises a hydrocarbon gas, e.g., methane or ethane. The film formed in the vapor deposition process using a precursor of the present disclosure may comprise silicon, e.g., cobalt silicate, as produced by a cobalt precursor containing silicon, and a co-reactant comprising at least one of water, $O_2$, $O_3$ and $N_2O$.

The cobalt deposition using the cobalt precursors of the present disclosure may be conducted in a process for manufacturing an integrated circuit or other product, e.g., a microprocessor, logic device, or a memory device.

The present disclosure also contemplates a method of providing for use in a vapor deposition process for depositing cobalt, a packaged cobalt precursor, wherein the cobalt precursor is selected from the group consisting of:

(a) cobalt hexacarbonyl complex precursors of the formula:

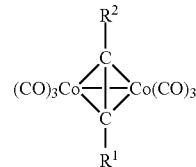

wherein $R^1$ and $R^2$ may be the same as or different from one another, and each is independently selected from among H, $C_1$-$C_4$ alkyl, silyl-substituted alkyl, dialkylamide, ethylene, acetylene, alkynes, substituted alkenes, $C_1$-$C_4$ substituted alkynes, silylalkyl, silylamide, trimethylsilyl, trialkylsilyl-substituted alkynes, and trialkylsilylamido-substituted alkynes, and wherein $R^1$ and $R^2$ are not both H;

(b) cobalt silylamide precursors;

(c) cobalt (0) carbonyl complex precursors including at least one ligand selected from the group consisting of alkenes, allenes, alkynes, and Lewis base ligands;

(d) cobalt hexacarbonyl dinitrile precursors of the formula [RN≡C—Co(CO)$_3$]$_2$, wherein R is independently selected from among H, $C_1$-$C_4$ alkyl, silyl-substituted alkyl, dialkylamide, ethylene, acetylene, alkynes, substituted alkenes, $C_1$-$C_4$ substituted alkynes, silylalkyl, silylamide, trimethylsilyl, trialkylsilyl-substituted alkynes, and trialkylsilylamido-substituted alkynes; and (e) cobalt dicarbonyl nitrile precursors of the formula (CO)$_2$CoN═O(C≡NR) wherein R is independently selected from among H, $C_1$-$C_4$ alkyl, silyl-substituted alkyl, dialkylamide, ethylene, acetylene, alkynes, substituted alkenes, $C_1$-$C_4$ substituted alkynes, silylalkyl, silylamide, trimethylsilyl, trialkylsilyl-substituted alkynes, and trialkylsilylamido-substituted alkynes.

In such method, the packaged precursor can comprise a precursor storage and dispensing vessel of suitable type, containing the cobalt precursor. The method may further comprise supplying for use in the vapor deposition process with the cobalt precursor a packaged co-reactant, e.g., a co-reactant as described hereinabove.

The disclosure in another aspect relates to a cobalt precursor selected from the group consisting of:

(a) cobalt hexacarbonyl complex precursors of the formula:

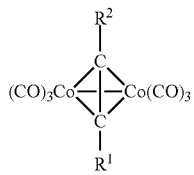

wherein $R^1$ and $R^2$ may be the same as or different from one another, and each is independently selected from among H, $C_1$-$C_4$ alkyl, silyl-substituted alkyl, dialkylamide, ethylene, acetylene, alkynes, substituted alkenes, $C_1$-$C_4$ substituted alkynes, silylalkyl, silylamide, trimethylsilyl, trialkylsilyl-substituted alkynes, and trialkylsilylamido-substituted alkynes, and wherein $R^1$ and $R^2$ are not both H;

(b) cobalt (0) carbonyl complex precursors including at least one ligand selected from the group consisting of alkenes, allenes, alkynes, and Lewis base ligands;

(c) cobalt hexacarbonyl dinitrile precursors of the formula $[RN\equiv C\text{---}Co(CO)_3]_2$, wherein R is independently selected from among H, $C_1$-$C_4$ alkyl, silyl-substituted alkyl, dialkylamide, ethylene, acetylene, alkynes, substituted alkenes, $C_1$-$C_4$ substituted alkynes, silylalkyl, silylamide, trimethylsilyl, trialkylsilyl-substituted alkynes, and trialkylsilylamido-substituted alkynes; and (d) cobalt dicarbonyl nitrile precursors of the formula $(CO)_2CoN\equiv O(C\equiv NR)$ wherein R is independently selected from among H, $C_1$-$C_4$ alkyl, silyl-substituted alkyl, dialkylamide, ethylene, acetylene, alkynes, substituted alkenes, $C_1$-$C_4$ substituted alkynes, silylalkyl, silylamide, trimethylsilyl, trialkylsilyl-substituted alkynes, and trialkylsilylamido-substituted alkynes.

The cobalt precursors may be of a specific class or classes, as variously described herein.

Cobalt silylamide and substituted carbonyl precursors of the present disclosure can be used to form conformal films, as required for high aspect-ratio features encountered in high density and high performance IC devices. Such cobalt films can be used in microprocessor, logic and memory devices where high-quality thin films are needed. Further, the low temperature precursors of the present disclosure enable deposition of cobalt on thermally sensitive substrates, such as may be encountered in flexible substrates, flat-panel displays, mobile devices and other portable computing applications.

Cobalt silylamide and cobalt carbonyl precursors of the present disclosure that are in solid form can be used in solid delivery systems, such as the ProE-Vap system commercially available from ATMI, Inc, Danbury, Conn., USA. The precursors may also be dissolved in appropriate solvents, e.g., hydrocarbon solvents, which facilitate liquid delivery of the precursor using liquid delivery systems coupled with a deposition reactor. The precursors can be used in liquid form, e.g., with direct liquid injection (DLI) systems, standard bubblers and modified bubblers. Delivery methods of widely varied character may be employed.

The use of any solvent or precursor solution, however, requires chemical compatibility with the cobalt silylamide or carbonyl complex precursor, thereby avoiding any deleterious reaction or premature decomposition of the precursor when dissolved in the solvent.

The precursors of the present disclosure can be packaged in any suitable manner, for storage and subsequent dispensing of the precursor for use.

Figure 5:
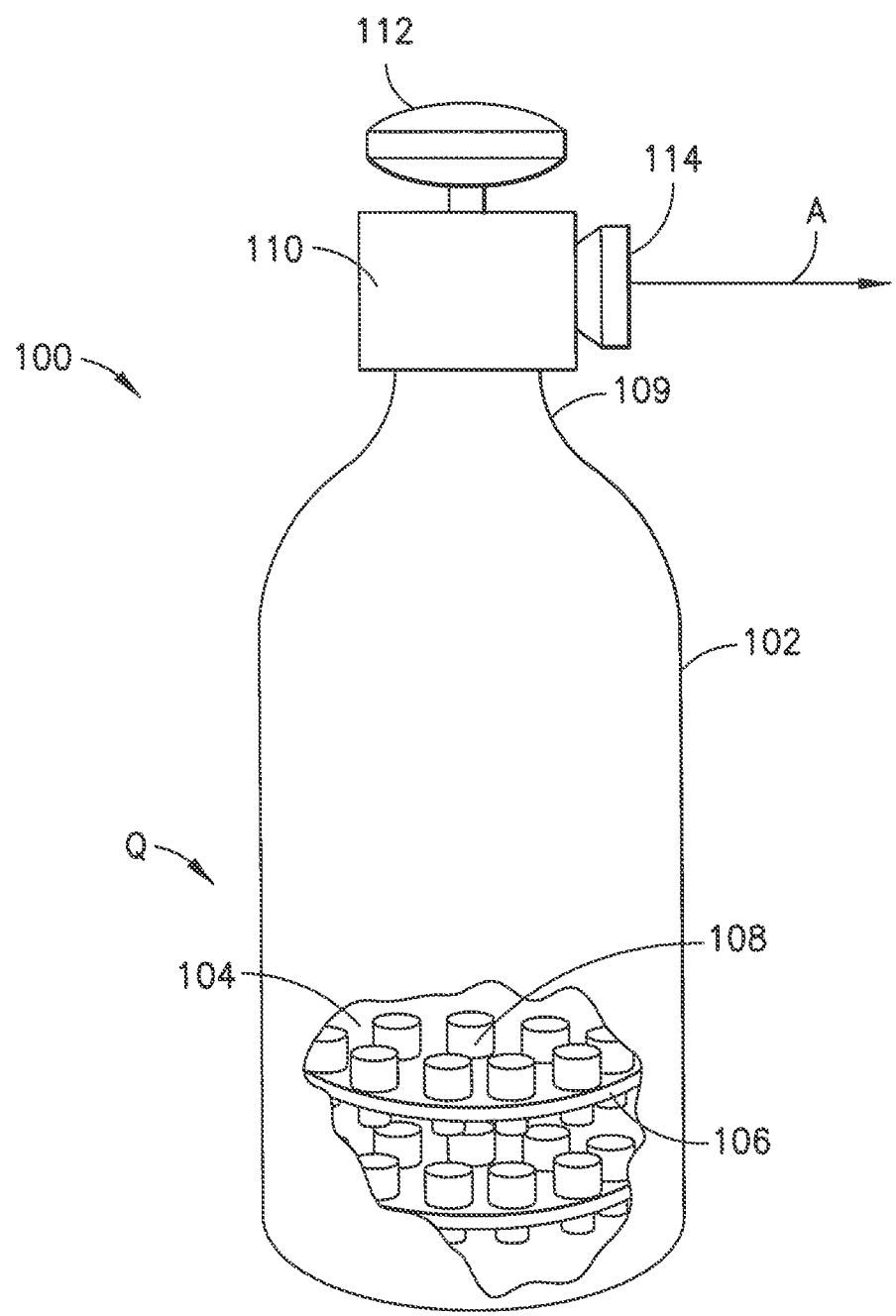
FIG. 5 is a schematic representation of a material storage and dispensing package containing a cobalt precursor, according to one embodiment of the present disclosure.

FIG. 5 is a schematic representation of an illustrative cobalt precursor storage and dispensing package 100 containing a cobalt precursor, according to one embodiment of the present disclosure.

The material storage and dispensing package 100 includes a vessel 102 that may for example be of generally cylindrical shape as illustrated, defining an interior volume 104 therein. In this embodiment, the cobalt precursor is a solid at ambient temperature conditions, and such precursor may be supported on surfaces of the trays 106 disposed in the interior volume 104 of the vessel, with the trays having flow passage conduits 108 associated therewith, for flow of vapor upwardly in the vessel to the valve head assembly, for dispensing in use of the vessel.

The solid precursor can be coated on interior surfaces in the interior volume of the vessel, e.g., on the surfaces of the trays 106 and conduits 108. Such coating may be effected by introducing the precursor into the vessel in a vapor form from which the solid precursor is condensed in a film on the surfaces in the vessel. Alternatively, the precursor solid may be dissolved or suspended in a solvent medium and deposited on surfaces in the interior volume of the vessel by solvent evaporation. In yet another method the precursor may be melted and poured onto the surfaces in the interior volume of the vessel, to solidify on the internal surfaces for subsequent volatilization as the solid material is heated, e.g., by flow of heated carrier gas through the vessel, and/or external heating of the vessel. For such purpose, the vessel may contain substrate articles or elements that provide additional surface area in the vessel for support of the precursor film thereon.

As a still further alternative, the solid precursor may be provided in granular or finely divided form, which is poured into the vessel to be retained on the top supporting surfaces of the respective trays 106 therein.

The vessel 102 has a neck portion 109 to which is joined the valve head assembly 110. The valve head assembly is equipped with a hand wheel 112 in the embodiment shown, but may alternatively employ an automatic valve actuator coupled to an automatic control system. The valve head assembly 110 includes a dispensing port 114, which may be configured for coupling to a fitting or connection element to join flow circuitry to the vessel. Such flow circuitry is schematically represented by arrow A in FIG. 1, and the flow circuitry may be coupled to a downstream ALD or CVD chamber or other cobalt precursor-utilizing system (not shown in FIG. 1).

In use, the vessel 102 is heated, such input of heat being schematically shown by the reference arrow Q, so that solid precursor in the vessel is at least partially volatilized to provide precursor vapor. The precursor vapor is discharged from the vessel through the valve passages in the valve head assembly 110 when the hand wheel 112 is translated to an open valve position, whereupon vapor deriving from the precursor is dispensed into the flow circuitry schematically indicated by arrow A.

In lieu of solid delivery of the precursor, the precursor may be provided in a solvent medium, forming a solution or suspension. Such precursor-containing solvent composition then may be delivered by liquid delivery and flash vaporized to produce a precursor vapor. The precursor vapor is contacted with a substrate under deposition conditions, to deposit the cobalt on the substrate in a film thereon.

In one embodiment, the precursor is dissolved in an ionic liquid medium, from which precursor vapor is withdrawn from the ionic liquid solution under dispensing conditions.

It will be recognized that the cobalt precursors of the present disclosure may be packaged in a variety of suitable vessels for dispensing of precursor material to a downstream precursor-utilizing process tool or facility, and that precursors of the present disclosure can be employed for a wide variety of end-use applications requiring cobalt deposition.

While the disclosure has been set out herein in reference to specific aspects, features and illustrative embodiments, it will be appreciated that the utility of the disclosure is not thus limited, but rather extends to and encompasses numerous other variations, modifications and alternative embodiments, as will suggest themselves to those of ordinary skill in the field of the present disclosure, based on the description herein. Correspondingly, the invention as hereinafter claimed is intended to be broadly construed and interpreted, as including all such variations, modifications and alternative embodiments, within its spirit and scope.

What is claimed is:

1. A cobalt precursor selected from the group consisting of:
   (a)

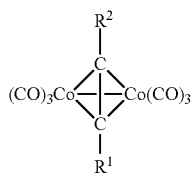

cobalt (0) carbonyl complex precursors including at least one ligand selected from the group consisting of allenes and Lewis base ligands; and (b) cobalt dicarbonyl nitrile precursors of the formula $(CO)_2CoN \equiv O(C \equiv NR)$ wherein R is independently selected from among H, dialkylamide, ethylene, acetylene, alkynes, substituted alkenes, $C_1$-$C_4$ substituted alkynes, silylamide, trimethylsilyl, trialkylsilyl-substituted alkynes, and trialkylsilylamido-substituted alkynes.

2. The cobalt precursor of claim 1, comprising a cobalt (0) carbonyl complex precursor including a Lewis base ligand.

3. A cobalt precursor comprising dicobalt hexacarbonyl (trimethylsilylacetylene).

4. A cobalt precursor comprising a cobalt hexacarbonyl dinitrile precursor of the formula $[RN \equiv C-Co(CO)_3]_2$, wherein R is independently selected from among H, $C_1$-$C_4$ alkyl, silyl-substituted alkyl, dialkylamide, ethylene, acetylene, alkynes, substituted alkenes, $C_1$-$C_4$ substituted alkynes, silylalkyl, silylamide, trimethylsilyl, trialkylsilyl-substituted alkynes, and trialkylsilylamido-substituted alkynes.

5. The cobalt precursor of claim 4, wherein the cobalt precursor comprises $[^tBuNC\ Co(CO)_3]_2$,

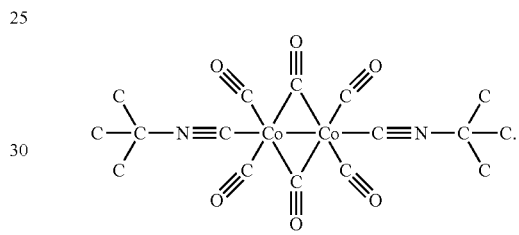

6. The cobalt precursor of claim 1, comprising a cobalt dicarbonyl nitrile precursor of the formula $(CO)_2CoN \equiv O(C \equiv NR)$ wherein R is independently selected from among H, ethylene, acetylene, alkynes, substituted alkenes, and $C_1$-$C_4$ substituted alkynes.

* * * * *